US00PP14611P29

(12) United States Plant Patent
Noodelijk

(10) Patent No.: US PP14,611 P2
(45) Date of Patent: Mar. 16, 2004

(54) CHRYSANTHEMUM PLANT NAMED 'CERES'

(50) Latin Name: *Chrysanthemum morifolium*
Varietal Denomination: Ceres

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 67 days.

(21) Appl. No.: 10/317,045

(22) Filed: Dec. 12, 2002

(51) Int. Cl.[7] ..... A01H 5/00
(52) U.S. Cl. ..... Plt./287
(58) Field of Search ..... Plt./287

*Primary Examiner*—Anne Marie Grunberg
(74) *Attorney, Agent, or Firm*—Parkhurst & Wendel, L.L.P.

(57) ABSTRACT

A chrysanthemum plant named 'Ceres' characterized by its medium sized blooms with pink ray florets and prolific branching; natural season flower date September 1–7; blooming for a period of 6 weeks.

3 Drawing Sheets

BACKGROUND OF THE INVENTION

'Ceres' is a product of a breeding and selection program for outdoor pot mums (garden mums) which had the objective of creating new chrysanthemum cultivars with a decorative type flower, a natural season flower date around September 1–7; blooming for a period of 6 weeks. The new plant of the present invention comprises a new and distinct cultivar of Chrysanthemum plant. 'Ceres' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout Holland in September 2000. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
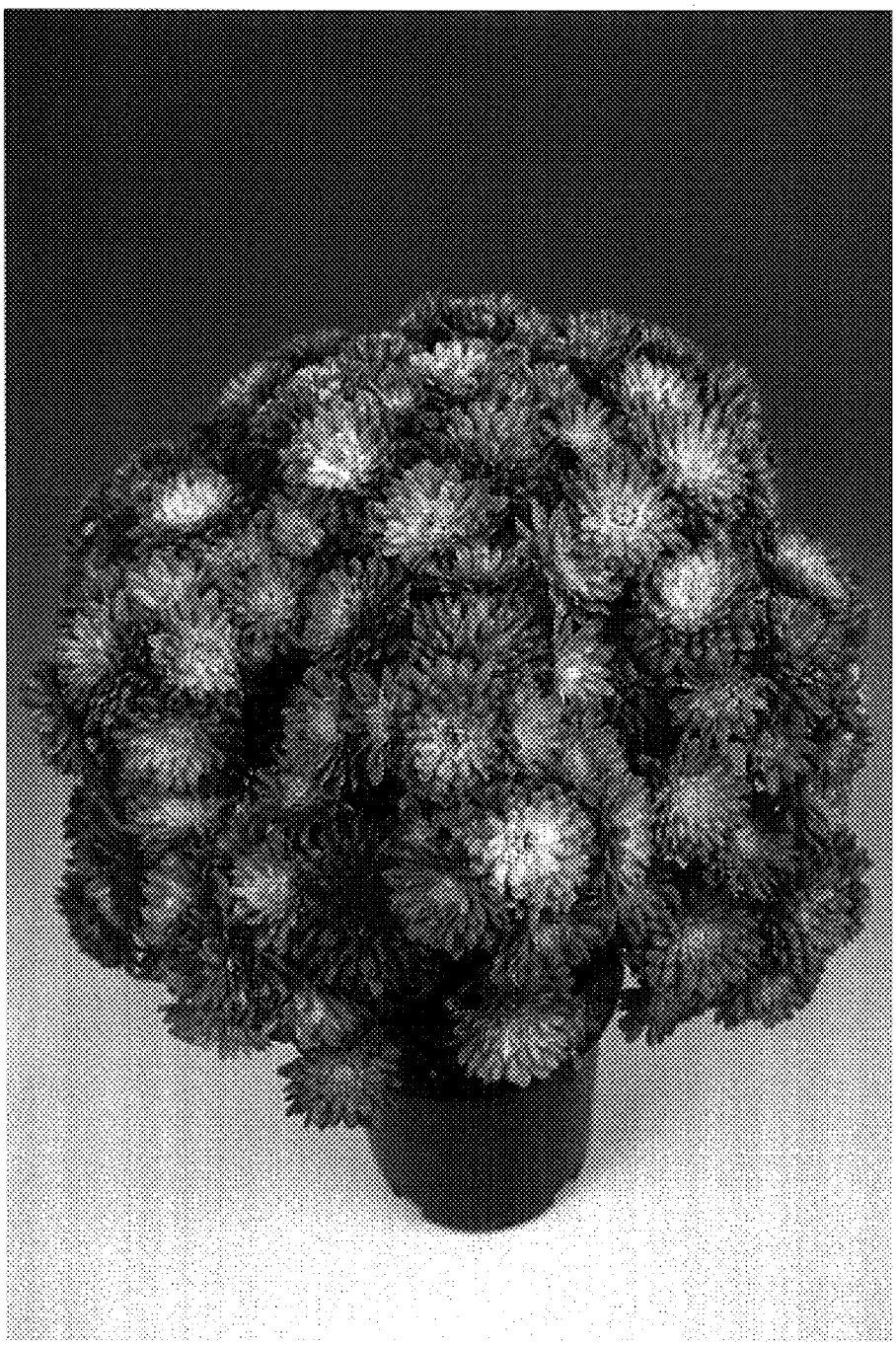
FIG. 1 shows a plant of the cultivar in full bloom.
Figure 2:
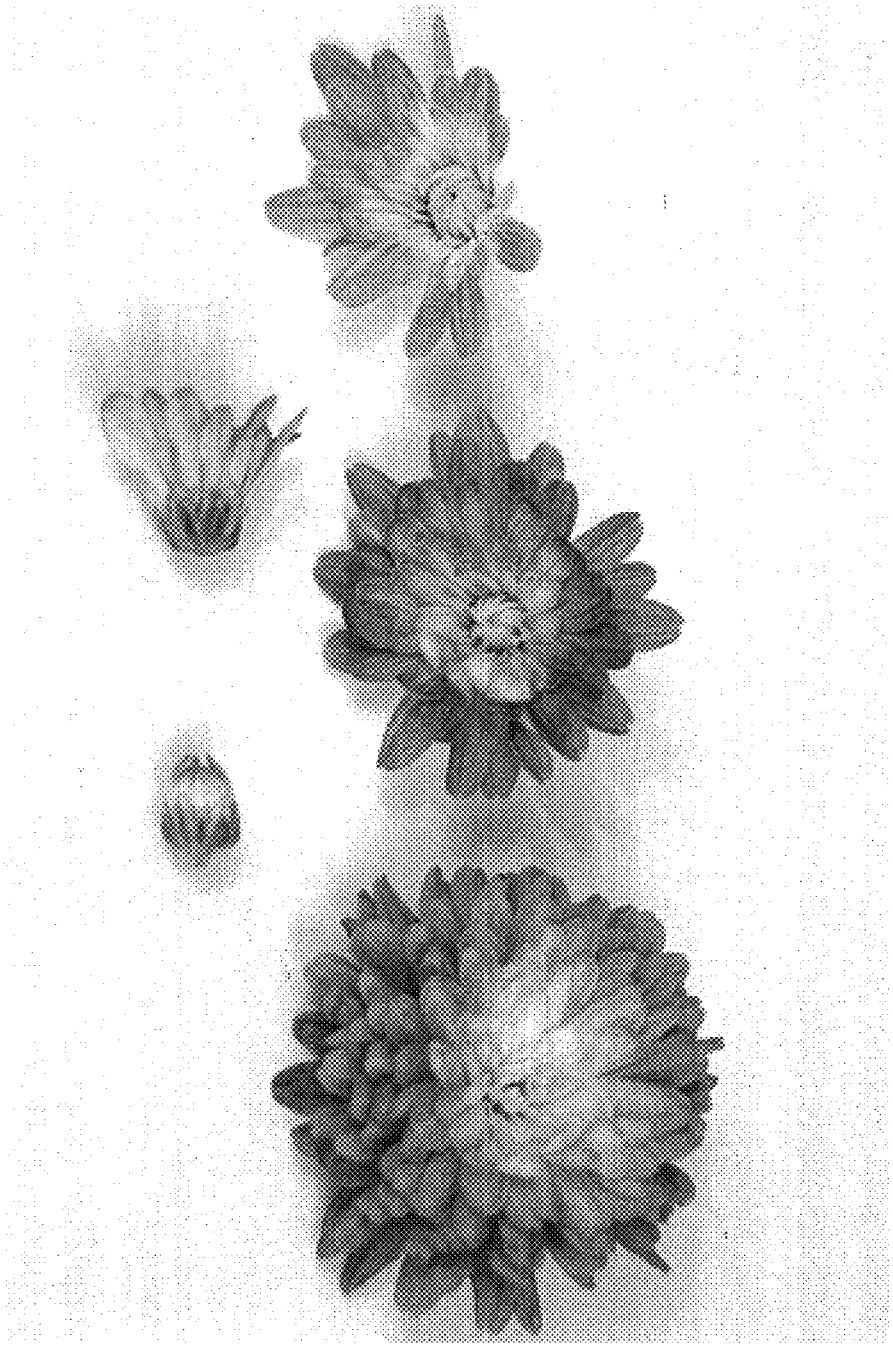
FIG. 2 shows the various stages of bloom of the new cultivar.
Figure 3:
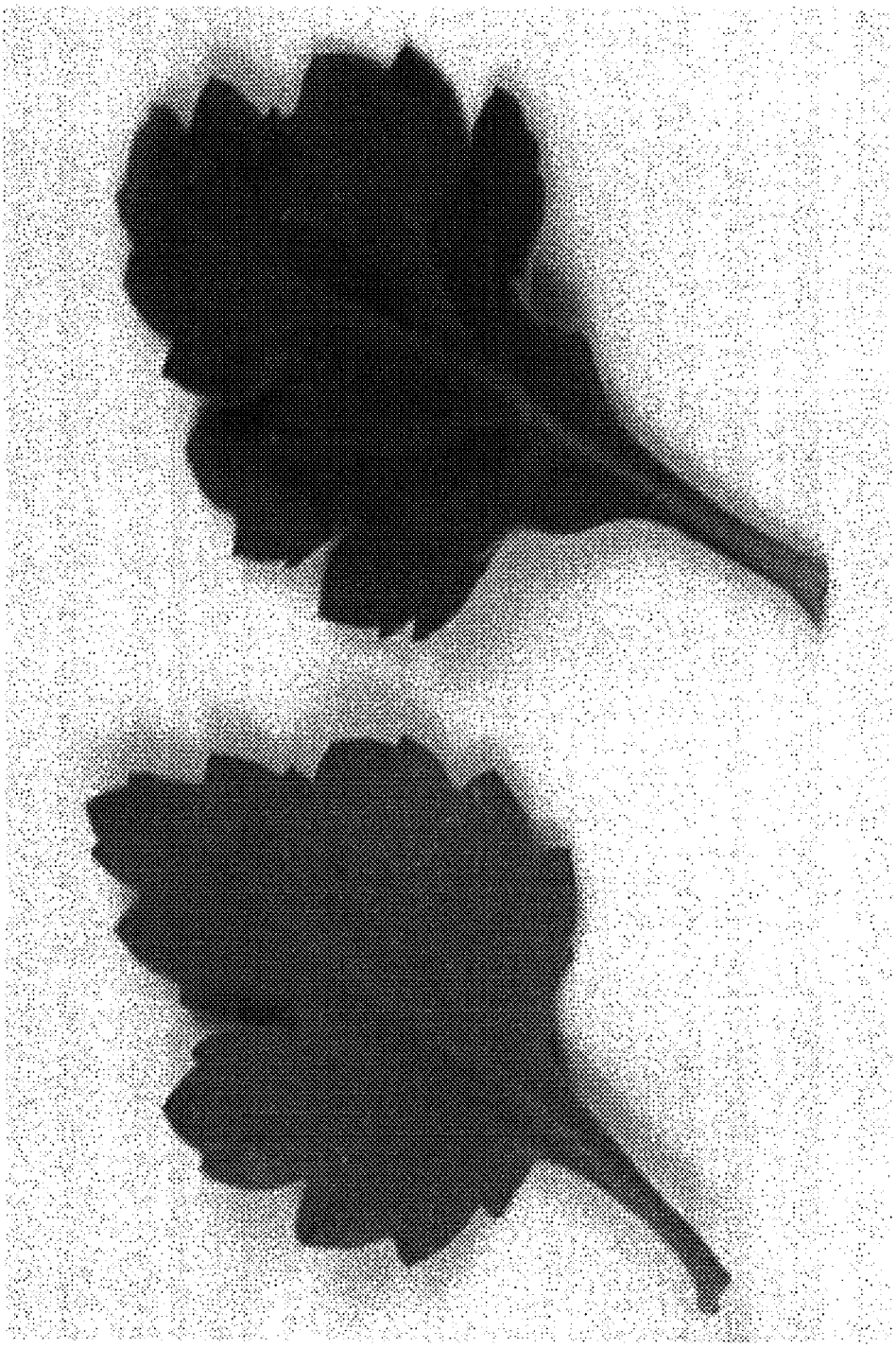
FIG. 3 shows the petiole and foliage of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 2000 And 2001. The natural blooming date of this crop was September 1–7 (week 36). The average height of the plants was 35 cm. No growth retardants were used. No tests were done on disease or insect resistance or susceptibility. No tests were done on cold or drought tolerance. This new variety produces medium sized blooms with pink ray florets and a cream center blooming for a period of 6 weeks.

From the cultivars known to inventor the most similar existing cultivar in comparison to 'Ceres' is 'Amata' (U.S. Plant patent application Ser. No. 10/317,052). The flower form of both cultivars looks similar. When 'Amata' and 'Ceres' are being compared the following differences are noticed: The differences of 'Amata' and 'Ceres' are (1) Flower color. The center of the flowers of 'Ceres' is orange-white and of 'Amata' is red. (2) Foliage shape. The shape of 'Ceres' is round and of 'Amata' is elliptic. (3) Foliage color. The color of 'Ceres' is more green than of 'Amata'.

The following is a description of the plant and characteristics that distinguish 'Ceres' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Table 1. Botanical Description of Cultivar 'Ceres'

Bud:
- *Size*.—Medium ;cross-section 1.0 cm, height 1.3 cm.
- *Outside color*.—White 155A, Red-Purple 62C at the tip.
- *Involucral bracts*.—2 rows, length 7 mm, width 3 mm.
- *Involucral bracts among disc-florets*.—Not present.
- *Involucral bracts color*.—Green 138A.

Bloom:
- *Type*. —Decorative.
- *Height*.—Medium, 1.5–1.7 cm.
- *Size*.—Medium.
- *Fully expanded*.—4.5–5.0 cm.
- *Number of blooms per branch*.—Approx. 6 blooms per branch.
- *Performance on the plant*.—6 weeks.
- *Seeds* (*if crossed*).—Not produced.
- *Fragrance*.—Typical chrysanthemum, slightly.

Color:
- *Center of the flower* (*without disc-florets*).—Immature orange-white 159A . Mature yellow-white 158B.
- *Color of upper surface of the ray-florets*.—Red-Purple 63B.

*Color of the lower surface of the ray-florets*.—Red-Purple 62D.
*Tonality from distance*.—A garden mum with pink flowers with a cream center.
*Color of the upper surface of the ray-florets after aging of the plant*.—Red-Purple 62 C.

Ray florets:
*Texture*.—Upper and under side smooth.
*Number*.—130–140.
*Cross-section*.—Concave.
*Longitudinal axis of majority*.—Straight.
*Length of corolla tube*.—Short, 0.2 cm.
*Ray-floret margin*.—Entire.
*Ray-floret length*.—1.8–2.0 cm.
*Ray-floret width*.—0.4–0.5 cm.
*Ratio length / width*.—Medium.
*Shape of tip*.—Round.

Disc florets: Not present.
Receptacle shape: Domed raised.
Reproductive organs:
*Stamen*.—Not present.
*Pollen*.—Not present.
*Style color*.—Yellow-green 144A.
*Style length*.—4 mm.
*Stigmas*.—Yellow-green 144A.
*Stigma width*.—1 mm.
*Ovaries*.—Enclosed in calyx.

Plant:
*Shape*.—Grown as a spray-type potmum, outdoor mounded and round.
*Growth habit*.—Spreading.
*Growth rate*.—Rapid.
*Height*.—35 cm.
*Width*.—40 cm.
*Stem color*.—Green 138A.
*Stem strength*.—Strong.
*Stem brittleness*.—Present.
*Stem anthocyanin coloration*.—Absent.
*Length of lateral branch*.—From top to bottom 12–13 cm.
*Lateral branch color*.—Green 138A.
*Lateral branch, attachment*.—Brittle.
*Branching* (*average number of lateral branches*).—Prolific with 8 breaks after pinching.
*Peduncle length*.—4.0–4.5 cm.
*Peduncle color*.—Green 138A.
*Natural season blooming date*.—September 1–7.

Foliage:
*Color*.—Upper side yellow-green 147A. Under side yellow-green 147C.
*Size*.—Small; length 4.0 cm, width 3.0 cm.
*Quantity* (*number per lateral branch*).—6.
*Shape*.—Oval.
*Texture upper side*.—Glabrous.
*Texture under side*.—Pubescent.
*Venation arrangement*.—Palmate.
*Shape of the margin*.—Serrated.
*Shape of base of sinus between lateral lobes*.—Acute.
*Margin of sinus between lateral lobes*.—Diverging.
*Shape of base*.—Rounded.
*Apex*.—Mucronate.

TABLE 2

Differences with the comparison varieties

| | 'CERES' | 'AMATA' |
|---|---|---|
| Color of the center of the flower | Orange-white 159A | Red 53D with a small dot of greyed-yellow 162C |
| Shape of the foliage | Round | Elliptic |
| Color of the foliage | Green 137A | Yellow-green 147A |

I claim:

1. A new and distinct variety of chrysanthemum plant as described and illustrated.

* * * * *